US011826567B2

(12) United States Patent
Samejima et al.

(10) Patent No.: US 11,826,567 B2
(45) Date of Patent: Nov. 28, 2023

(54) ELECTRICAL TREATMENT DEVICE, CONTROL METHOD, AND TREATMENT SYSTEM

(71) Applicant: OMRON HEALTHCARE Co., Ltd., Kyoto (JP)

(72) Inventors: Mitsuru Samejima, Kyoto (JP); Yui Watanabe, Kyoto (JP); Shozo Takamatsu, Kyoto (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 729 days.

(21) Appl. No.: 16/860,171

(22) Filed: Apr. 28, 2020

(65) Prior Publication Data

US 2020/0254253 A1  Aug. 13, 2020

Related U.S. Application Data

(63) Continuation of application No. PCT/JP2018/039032, filed on Oct. 19, 2018.

(30) Foreign Application Priority Data

Nov. 6, 2017  (JP) ................................. 2017-213778

(51) Int. Cl.
*A61N 1/36* (2006.01)
*A61N 1/04* (2006.01)

(52) U.S. Cl.
CPC ....... *A61N 1/36034* (2017.08); *A61N 1/0452* (2013.01); *A61N 1/0492* (2013.01); *A61N 1/36003* (2013.01); *A61N 1/36021* (2013.01)

(58) Field of Classification Search
CPC ....................... A61N 1/36034; A61N 1/36139
See application file for complete search history.

(56) References Cited

U.S. PATENT DOCUMENTS 6,631,297 B1  10/2003  Mo
2004/0230253 A1  11/2004  Sakagami et al.
(Continued)

FOREIGN PATENT DOCUMENTS

| JP | 2000-14803 A | 1/2000 |
| JP | 2002248175 A | 9/2002 |

(Continued)

OTHER PUBLICATIONS

International Search Report of the International Searching Authority for PCT/JP2018/039032 dated Jan. 15, 2019.
(Continued)

*Primary Examiner* — Alyssa M Alter
(74) *Attorney, Agent, or Firm* — Birch, Stewart, Kolasch & Birch, LLP (57) ABSTRACT

An electrical treatment device (200) includes a treatment content setting unit (302), a treatment execution unit (306), and an output control unit (304) that outputs a pulse voltage at a first frequency within a predetermined frequency range before treatment of a site is performed by the treatment execution unit (306). When the pulse voltage is output at the first frequency, the treatment content setting unit (302) receives input of an electrical stimulation intensity desired by a user. The treatment execution unit (306) executes the treatment of the site by varying the pulse voltage corresponding to the electrical stimulation intensity desired by the user within the predetermined frequency range.

16 Claims, 7 Drawing Sheets

(56) References Cited

U.S. PATENT DOCUMENTS

2009/0069864 A1     3/2009   Sakagami et al.
2013/0289667 A1* 10/2013   Wacnik .............. A61N 1/36171
                                                                                                                                                               607/2

FOREIGN PATENT DOCUMENTS

| JP | 2004337298 A | 12/2004 |
|----|--------------|---------|
| JP | 2005168642 A | 6/2005 |
| JP | 2005252449 A | 9/2005 |
| JP | 2016073372 A | 5/2016 |

OTHER PUBLICATIONS

Translation of the International Search Report of the International Searching Authority for PCT/JP2018/039032 dated Jan. 15, 2019.
German Office Action for German Application No. 112018004703.2, dated Feb. 4, 2022, with an English translation.
International Preliminary Report on Patentability (Chapter II) of the International Preliminary Examining Authority for PCT/JP2018/039032 with search date of Jun. 5, 2019.
English translation of International Preliminary Report on Patentability (Chapter II) of the International Preliminary Examining Authority for PCT/JP2018/039032 with search date of Jun. 5, 2019.

* cited by examiner

ELECTRICAL TREATMENT DEVICE, CONTROL METHOD, AND TREATMENT SYSTEM

CROSS-REFERENCE TO RELATED APPLICATIONS

This is a continuation of International Application PCT/JP2018/039032, with an international filing date of Oct. 19, 2018, and 2017-213778 with an international filing date of Nov. 6, 2017, and filed by applicant, the disclosure of which is hereby incorporated by reference in its entirety.

TECHNICAL FIELD

The present disclosure relates to an electrical treatment device, a control method, and a treatment system.

BACKGROUND ART

There are known electrical devices that alleviate stiffness and pain. Such electrical treatment devices provide stimulation by outputting an electrical signal to muscles via an electrode placed in contact with the surface of the body, such as on the abdomen or the back.

For example, JP 2005-168642 A (Patent Document 1) describes an electrical stimulation device. This electrical stimulation device detects the output of each output unit while performing stimulation by changing such as the frequency and the waveform of the stimulation signal and continuously controls the output to keep it at a predetermined value.

CITATION LIST

Patent Literature

Patent Document 1: JP 2005-168642 A

SUMMARY OF INVENTION

Technical Problem

The electrical stimulation device according to Patent Document 1 performs stimulation with a stimulation signal of varying frequency. In this manner, with the electrical stimulation varying in frequency within a predetermined frequency range, the user feels a varying degree of electrical stimulation. As such, an electrical stimulation at a certain frequency within the predetermined frequency range may provide an electrical stimulation to the user that is unintended (for example, a stimulation that is too strong) and cause discomfort to the user. Patent Document 1 does not explain nor suggest any technology for solving this problem.

An object of an aspect of the present disclosure is to provide an electrical treatment device, a control method, and a treatment system that can perform a comfortable treatment for the user with a pulse voltage of varying frequency being provided to the user during treatment.

Solution to Problem

One example of the present disclosure includes a treatment content setting unit configured to set a treatment content specified by a user, a treatment execution unit configured to perform treatment of a site on a body of the user according to the treatment content by controlling a pulse voltage applied to a plurality of electrodes being in contact with the site, and an output control unit configured to output a pulse voltage at a first frequency within a predetermined frequency range before the site being performed the treatment by the treatment execution unit. When the pulse voltage at the first frequency is output, the treatment content setting unit receives an input of an electrical stimulation intensity desired by the user. The treatment execution unit executes the treatment of the site by varying a pulse voltage corresponding to the electrical stimulation intensity desired by the user within the predetermined frequency range.

This configuration can perform a comfortable treatment for the user with a pulse voltage of varying frequency being provided to the user during treatment.

In another example of the present disclosure, the output control unit gradually increases the electrical stimulation intensity and outputs the pulse voltage corresponding to the electrical stimulation intensity at the first frequency.

According to this configuration, it is possible to adjust the electrical stimulation intensity used in treatment without causing discomfort to the user.

In another example of the present disclosure, the first frequency is a maximum frequency within the predetermined frequency range or a frequency within a range of from 20 Hz to 60 Hz.

According to this configuration, the treatment can be performed without causing discomfort due to too strong electrical stimulation to the user during treatment or without causing discomfort to the user due to the occurrence of muscle contraction during treatment.

In another example of the present disclosure, when the pulse voltage is output at the first frequency, the treatment content setting unit receives input of a first electrical stimulation intensity desired by the user. The output control unit outputs a pulse voltage corresponding to the first electrical stimulation intensity at a second frequency within the frequency range. When a pulse voltage corresponding to the first electrical stimulation intensity is output at the second frequency and execution of treatment of the site using the first electrical stimulation intensity is allowed by the user, the treatment execution unit performs the treatment of the site by varying the pulse voltage corresponding to the first electrical stimulation intensity within the frequency range.

According to this configuration, a treatment more comfortable for the user can be performed.

In another example of the present disclosure, the first frequency is a maximum frequency within the predetermined frequency range. The second frequency is a frequency within a range of from 20 Hz to 60 Hz.

According to this configuration, the treatment can be performed without causing discomfort due to too strong electrical stimulation to the user during treatment and without causing discomfort to the user due to the occurrence of muscle contraction during treatment.

In another example of the present disclosure, the treatment execution unit varies the frequency of the pulse voltage by sweeping the frequency in increasing direction from a minimum frequency to a maximum frequency, then in decreasing direction from the maximum frequency to the minimum frequency in the frequency range.

According to this configuration, the electrical stimulation felt by the user is gradually increased, which makes it possible to further reduce the possibility of causing discomfort to the user.

In another example of the present disclosure, the electrical treatment device is a low-frequency treatment device.

According to this configuration, the user can receive treatment in a more appropriate frequency range.

In another example of the present disclosure, a control method of an electrical treatment device includes the steps of setting a treatment content specified by a user, executing treatment of a site on a body of the user according to the treatment content by controlling a pulse voltage applied to a plurality of electrodes being in contact with the site, and outputting a pulse voltage at a first frequency within a predetermined frequency range before the site being performed the treatment in the executing step. When the pulse voltage at the first frequency is output, the setting step includes receiving an input of an electrical stimulation intensity desired by the user. The executing step includes performing the treatment of the site by varying a pulse voltage corresponding to the electrical stimulation intensity desired by the user within the predetermined frequency range.

This configuration can perform a comfortable treatment for the user with a pulse voltage of varying frequency being provided to the user during treatment.

In another example of the present disclosure, a treatment system includes a terminal device, and an electrical treatment device configured to be wirelessly communicative with the terminal device. The electrical treatment device includes a treatment content setting unit configured to set a treatment content specified by a user, a treatment execution unit configured to perform treatment of a site on a body of the user according to the treatment content by controlling a pulse voltage applied to a plurality of electrodes being in contact with the site, and an output control unit configured to output a pulse voltage at a first frequency within a predetermined frequency range before the site where the treatment by the treatment execution unit is performed. When the pulse voltage at the first frequency is output, the treatment content setting unit receives an input of an electrical stimulation intensity desired by the user through the terminal device. The treatment execution unit executes the treatment of the site by varying a pulse voltage corresponding to the electrical stimulation intensity desired by the user within the predetermined frequency range.

Advantageous Effects of Invention

The present disclosure can perform a comfortable treatment for the user with a pulse voltage of varying frequency being provided to the user during treatment.

DESCRIPTION OF EMBODIMENTS

Embodiments of the present invention will be described below with reference to the drawings. In the following description, like components are given like numerals. Names and functions thereof are also the same. Thus, the detailed description of such components is not repeated.

Application Example

Figure 1:
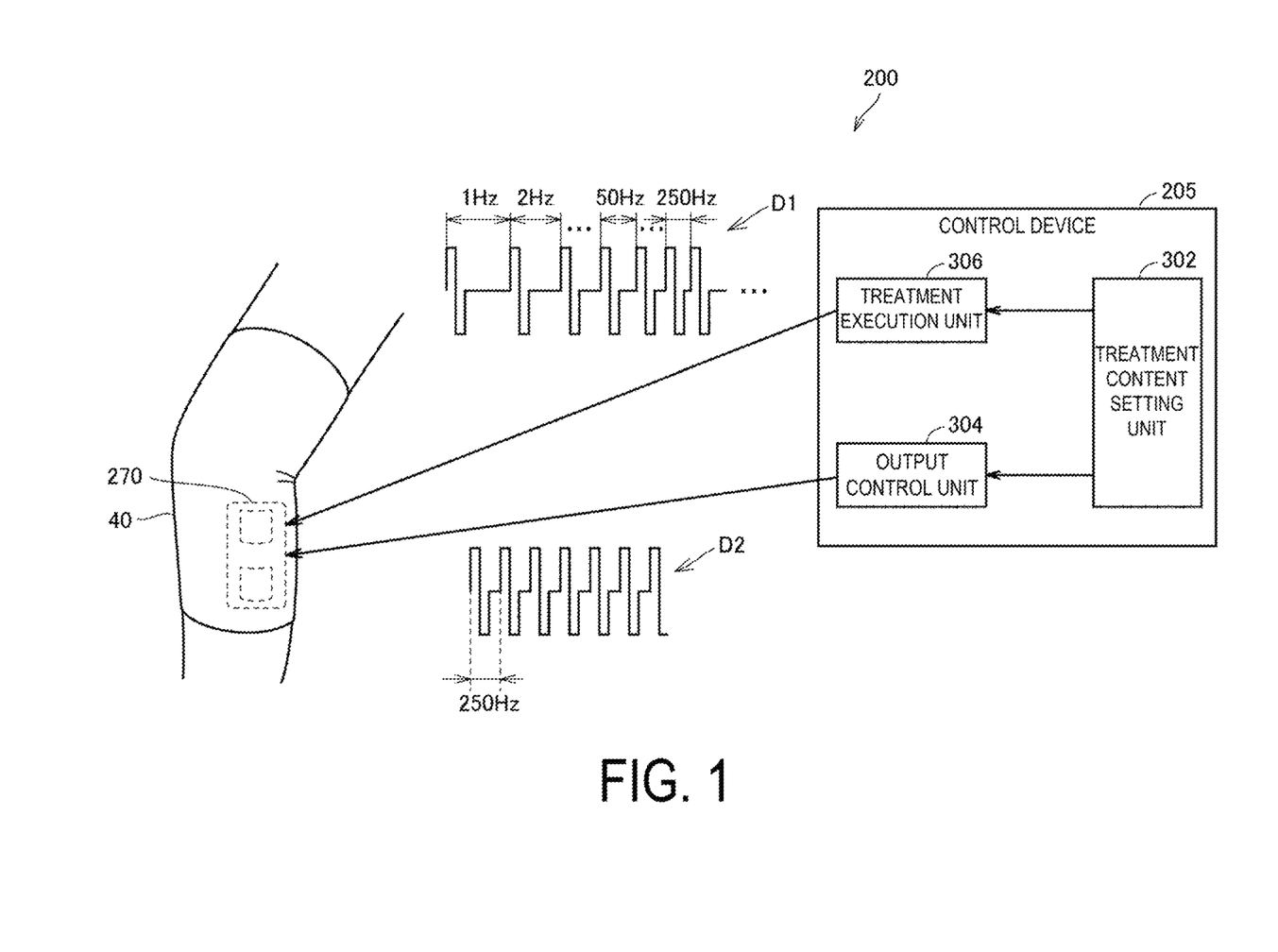
FIG. 1 is a diagram illustrating an electrical treatment device according to the present embodiment.

An application example of the present invention will be described with reference to FIG. 1. FIG. 1 is a diagram illustrating an electrical treatment device 200 according to the present embodiment.

Referring to FIG. 1, the electrical treatment device 200 includes a control device 205, i.e., a main body portion, and a pair of pads 270 that are stuck to the treatment site (for example, the knee region). The control device 205 and the pads 270 are electrically connected by a cord. A supporter 40 is a knee supporter that entirely covers the knee region of a user.

The electrical treatment device 200 is a low-frequency treatment device that performs treatment such as alleviating knee pain and easing shoulder stiffness of the user by supplying a low-frequency pulse, for example. The frequency of the low-frequency pulse current is, for example, from 1 Hz to 1200 Hz.

The pads 270 have a sheet-like shape and are configured to attach to the user's body. The surface on one side of the pad 270 (the surface that does not come into contact with the body) is provided with a plug that corresponds to an electrode (not illustrated) formed on the surface on the other side (the surface that comes into contact with the body). The electrode is formed from a conductive gel-like material, for example.

The control device 205 includes as main components, a treatment content setting unit 302, an output control unit 304, and a treatment execution unit 306. The treatment content setting unit 302 receives various instructions relating to the treatment content from the user and provides instructions to the output control unit 304 and the treatment execution unit 306.

The treatment execution unit 306 controls the pulse voltage applied to electrodes of the pair of pads 270 that come into contact with the site (for example, knee) on the body of the user according to a treatment instruction from the user and performs treatment on the knee. The treatment execution unit 306 outputs a pulse voltage with a frequency that repeatedly varies within a predetermined frequency range K (for example, from 1 Hz to 250 Hz) in a continuous or step-like manner.

For example, a voltage waveform D1 of the pulse voltage output by the treatment execution unit 306 is a sweep waveform that continuously increases from 1 Hz to 250 Hz then continuously decreases from 250 Hz to 1 Hz. For the electrical treatment device 200, the predetermined frequency range K (1 Hz to 250 Hz) is a frequency range preset for the electrical treatment device 200 and is used as the frequency range when performing treatment using a sweep waveform with a repeatedly varying frequency. Note that the amplitude, pulse width, and the like of the pulse voltage can be changed as appropriate depending on the selection instruction of the treatment mode and the adjustment instruction of the electrical stimulation intensity.

Typically, in the case where treatment is performed using a sweep waveform with a repeatedly varying frequency, a display and the like of the control device 205 is used to prompt the user to adjust the electrical stimulation intensity. The user provides an adjustment instruction for electrical stimulation intensity to the electrical treatment device 200.

The output control unit 304 outputs a pulse voltage in accordance with an adjustment instruction for the electrical stimulation intensity at a frequency Fs within the frequency range K before knee treatment starts by a pulse voltage output from the treatment execution unit 306. Typically, the frequency Fs is set to a frequency at which the user feels that the electrical stimulation is the strongest within the frequency range K. For example, in a case where the frequency range K is from 1 Hz to 250 Hz, the frequency Fs is set to 250 Hz, which is the maximum frequency. In this case, a voltage waveform D2 of the pulse voltage output by the output control unit 304 is a 250 Hz pulse waveform.

When the pulse voltage output by the output control unit 304 is 250 Hz, the treatment content setting unit 302 receives an input for a desired electrical stimulation intensity from the user and sets the received electrical stimulation intensity as the electrical stimulation intensity used in treatment. The treatment execution unit 306 executes knee treatment by varying the pulse voltage corresponding to the set electrical stimulation intensity within the frequency range K.

With the electrical treatment device 200 with the configuration described above, the user can adjust the electrical stimulation intensity to a desired intensity at a frequency at which the electrical stimulation is most likely to be felt before getting actual treatment of a sweep waveform with a repeatedly varying frequency. As such, the electrical stimulation can be prevented from being too strong and causing discomfort or surprising the user after treatment starts.

Also, in general, the frequency range in which muscles are prone to contract is from 20 Hz to 60 Hz. Also, muscle contraction is more likely to occur the greater the electrical stimulation intensity is. Thus, the above-described frequency Fs may be set to a frequency within a range of from 20 Hz to 60 Hz. In this case, the electrical stimulation intensity can be adjusted to a desired intensity at a frequency at which muscles are prone to contract within the frequency range K. As such, the muscles contracting can be prevented from occurring and causing discomfort or startling the user after treatment starts.

In this way, the electrical treatment device 200 can perform a comfortable treatment for the user with a pulse voltage of varying frequency being provided to the user during treatment.

Configuration Example

First Embodiment

Appearance

Figure 2:
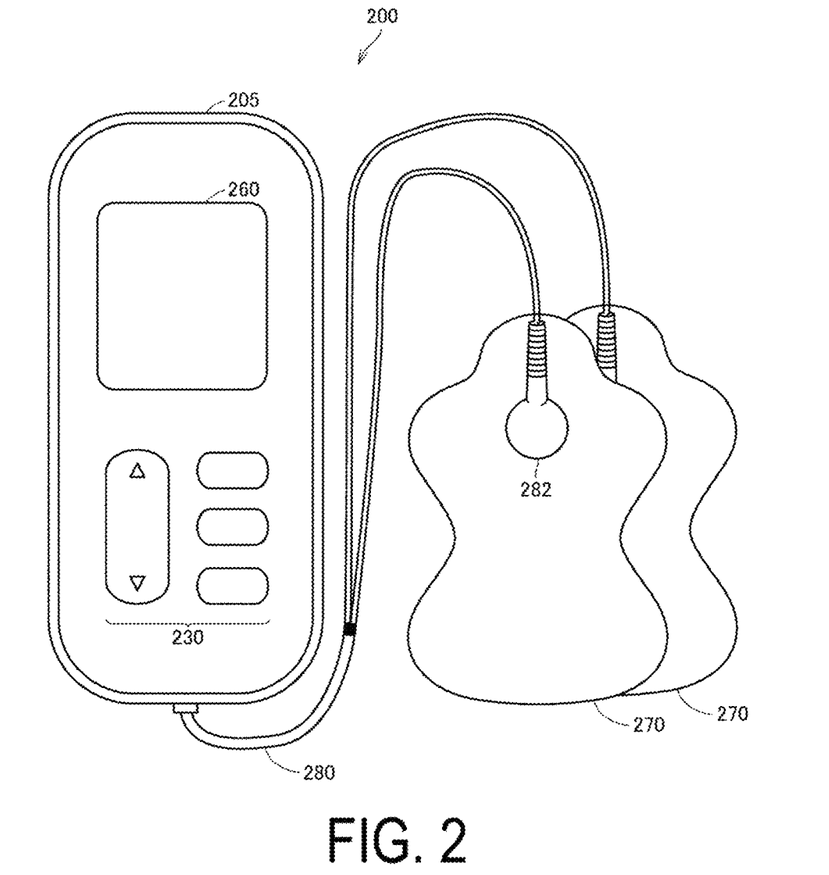
FIG. 2 is a diagram illustrating an example of the appearance of the electrical treatment device according to a first embodiment.

FIG. 2 is a diagram illustrating an example of the appearance of the electrical treatment device 200 according to the first embodiment. Referring to FIG. 2, the electrical treatment device 200 includes the control device 205, the pair of pads 270, and a cord 280 for electrically connecting the control device 205 and the pads 270.

The control device 205 and the pads 270 are connected together by connecting together a plug 282 of the cord 280 and the plug on the pad 270 and inserting the cord 280 into the jack of the control device 205. Note that when the polarity of the electrode formed on one of the pads 270 is positive, the polarity of the electrode formed on the other pad 270 is negative.

The control device 205 is provided with a display 260 and an input interface 230 constituted by various buttons. The input interface 230 includes a power button configured to switch the power on and off, a mode selection button configured to select a treatment mode, a treatment start button, an adjustment button configured to adjust the intensity of the electrical stimulation, and the like. Note that the input interface 230 is not limited to the configuration described above, and may be configured to enable various operations by the user as described below. The input interface 230 may be constituted by, for example, other buttons, dials, switches, and the like.

The electrical stimulation intensity, the remaining treatment time, the treatment mode, the mounting state of the pads 270, and the like are displayed on the display 260. Various messages are also displayed on the display 260.

Hardware Configuration

Figure 3:
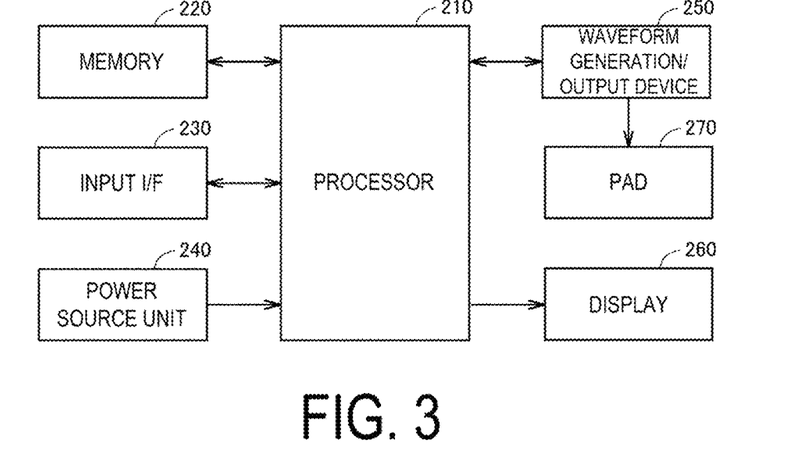
FIG. 3 is a block diagram illustrating an example of a hardware configuration of the electrical treatment device according to the first embodiment.

FIG. 3 is a block diagram illustrating an example of a hardware configuration of the electrical treatment device 200 according to the first embodiment. Referring to FIG. 3, the electrical treatment device 200 includes a processor 210, a memory 220, the input interface 230, a power source unit 240, a waveform generation/output device 250, and the display 260.

The processor 210 typically may be an arithmetic processing unit such as a central processing unit (CPU) or a multi processing unit (MPU). The processor 210 functions as a control unit that controls the operation of components of the electrical treatment device 200 by reading out and executing a program stored in the memory 220. By executing the program, the processor 210 realizes each of processing (steps) of the electrical treatment device 200 described later.

The memory 220 is realized by random access memory (RAM), read-only memory (ROM), flash memory, and the like. The memory 220 stores programs executed by the processor 210, data used by the processor 210, and the like.

The input interface 230 is constituted by various buttons such as those described above and receives an operation input for the electrical treatment device 200. When the user operates various buttons, a signal corresponding to the operation is input to the processor 210. [0047]

The power source unit 240 supplies power to the constituent elements of the electrical treatment device 200. As the power source, an alkaline battery or a rechargeable battery, such as a lithium ion battery or nickel hydrogen battery may be used, for example. The power source stabilizes a battery voltage and generates a drive voltage that is supplied to the components.

The waveform generation/output device 250 outputs a current (also referred to below as a "treatment current") to a treatment site on the user's body through the pads 270. The waveform generation/output device 250 includes a booster circuit, a voltage adjustment circuit, an output circuit, a current detection circuit, and the like.

The booster circuit boosts the power supply voltage to a predetermined voltage. The voltage adjustment circuit adjusts the voltage boosted by the booster circuit to a voltage corresponding to the electrical stimulation intensity set by the user. Specifically, the electrical stimulation of the electrical treatment device 200 can be adjusted to a predetermined number of levels (for example, ten levels) by an adjustment button. The processor 210 receives a setting input of the electrical stimulation intensity through the adjustment button and instructs the waveform generation/output device 250 (voltage adjustment circuit) to adjust to a voltage corresponding to the received electrical stimulation intensity.

The output circuit generates a treatment waveform (pulse waveform) corresponding to the treatment mode on the basis of the voltage adjusted by the voltage adjustment circuit and outputs the treatment waveform to (the electrodes of) the pads 270 via the cord 280. Specifically, when an operation, such as switching the treatment mode, changing the electrical stimulation intensity, or the like is performed by the user through the input interface 230, a control signal corresponding to the operation content is input to the output circuit from the processor 210. The output circuit outputs a treatment waveform according to the control signal.

In this example, the electrical treatment device 200 is provided with a plurality of treatment modes in advance. The treatment modes include, for example, "massage", "tap", "press", and "sweep".

The output circuit can generate an electrical stimulation corresponding to various modes including "massage", "tap", "press", and "sweep" by varying the waveform of the pulses (including pulse width, pulse interval, frequency, and output polarity). Also, by changing the amplitude of the pulse voltage, the output circuit adjusts the electrical stimulation intensity. Note that the output circuit may have a configuration in which the electrical stimulation intensity is adjusted by changing the pulse width. Specifically, a known voltage waveform can be used as the pulse voltage waveform.

Figure 4:
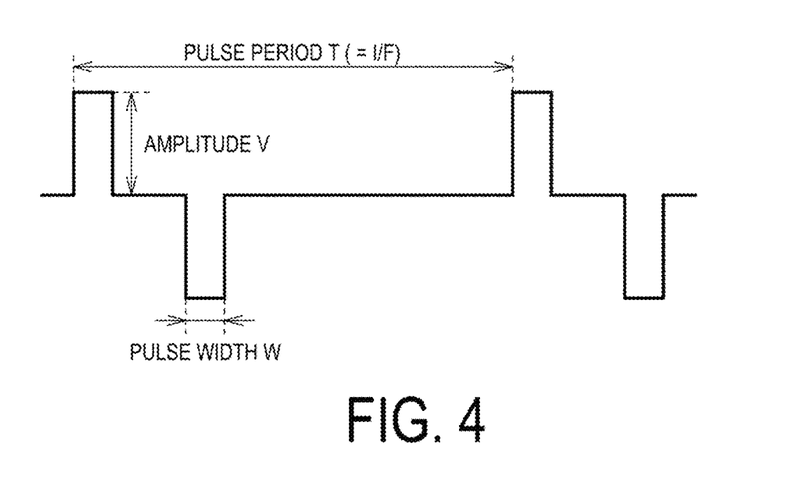
FIG. 4 is a diagram for describing parameters of a pulse voltage waveform.

FIG. 4 is a diagram for describing parameters of the pulse voltage waveform. Referring to FIG. 4, the parameters of the pulse voltage waveform include an amplitude (voltage) V, a pulse width W, and a pulse period T (i.e., pulse frequency F=1/T). The processor 210 can change the treatment content for the user by changing at least one parameter of the three parameters.

Referring again to FIG. 3, the current detection circuit detects a value for the current flowing between the pair of pads 270 and inputs a signal indicating the detected value to the processor 210. From the current value input from the current detection circuit, the processor 210 can detect whether the pads 270 are mounted (stuck) to the user or whether the pads 270 are not mounted to (fallen off from) the user.

Specifically, when the current value is a predetermined value or greater, the processor 210 decides that the electrodes are in contact (i.e., the pair of pads 270 are mounted to the user). When the current value is less than a predetermined value, the processor 210 decides that at least one of the electrodes is not in contact (at least one of the pair of pads 270 is not mounted to the user). This utilizes the principle that, in the case where at least one of the pair of pads 270 is not properly mounted to the user, a current loop, whereby the current output from one of the pads 270 returns to the other of the pads 270 through the human body, is not established, and thus a current of a predetermined value or greater does not flow.

The display 260 is constituted of, for example, a liquid crystal display (LCD) and displays various information in accordance with an instruction from the processor 210.

Functional Configuration

Figure 5:
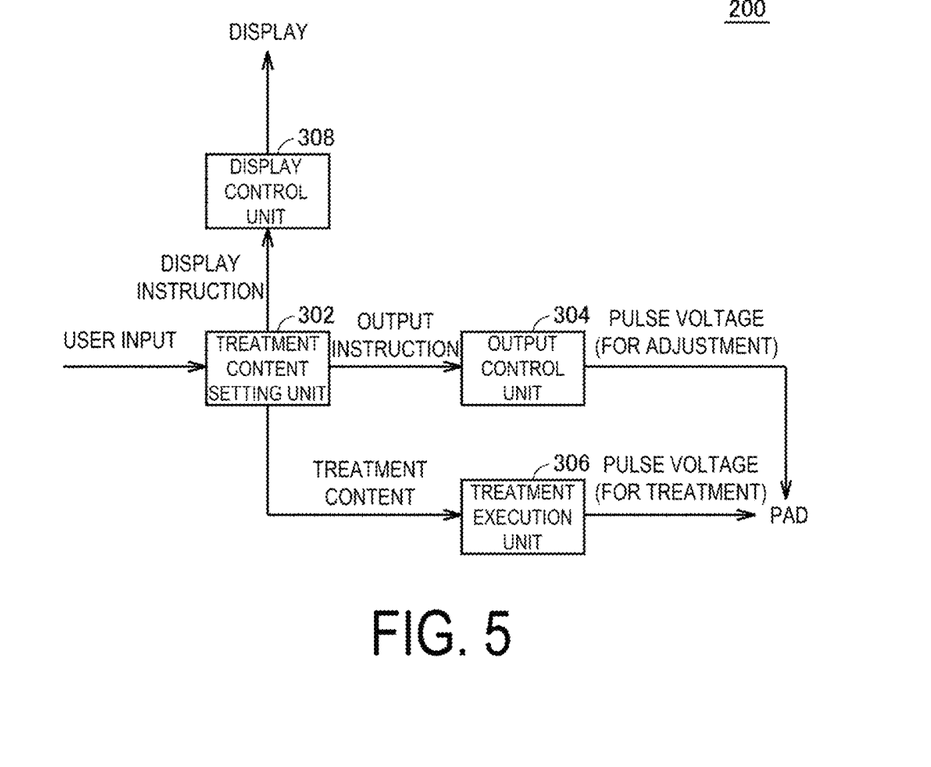
FIG. 5 is a block diagram illustrating an example of the functional configuration of the electrical treatment device according to the first embodiment.

FIG. 5 is a block diagram illustrating an example of the functional configuration of the electrical treatment device 200 according to the first embodiment. Referring to FIG. 5, the electrical treatment device 200 includes the treatment content setting unit 302, the output control unit 304, the treatment execution unit 306, and a display control unit 308.

The treatment content setting unit 302 sets the treatment content specified by the user. Specifically, the treatment content setting unit 302 receives a setting input of the treatment content through the input interface 230. The treatment content includes the treatment mode and the electrical stimulation intensity. The treatment content setting unit 302 may accept from the user a setting input for the treatment time, which is the amount of time for performing the treatment in accordance with the treatment content. However, the treatment time may be a preset fixed amount of time.

When the treatment content setting unit 302 determines that the treatment mode specified by the user is a treatment mode that uses a pulse voltage with a frequency that varies within the frequency range K (i.e., a mode using a sweep waveform), processing for adjusting the electrical stimulation intensity is executed.

Specifically, the treatment content setting unit 302 instructs the display control unit 308 to display a selection screen of adjustment patterns of the electrical stimulation intensity. The display control unit 308 causes the display 260 to display a selection screen of adjustment patterns. For example, the selection screen prompts the user to select pattern Pa of adjusting the electrical stimulation intensity by the output of a pulse voltage at a maximum frequency within the frequency range K or pattern Pb of adjusting the electrical stimulation intensity by the output of a pulse voltage at from 20 Hz to 60 Hz. For example, when the user feels discomfort from a too strong electrical stimulation, they may choose the pattern Pa, and when the user feels discomfort from occurrence of muscle contracting, they may choose the pattern Pb.

When the selection instruction of the pattern Pa is received through the input interface 230, the treatment content setting unit 302 instructs the output control unit 304 to output a pulse voltage at the maximum frequency. When the selection instruction of the pattern Pb is received, the treatment content setting unit 302 instructs the output control unit 304 to output a pulse voltage at a frequency within from 20 Hz to 60 Hz.

The output control unit 304 applies the pulse voltage for adjustment of the electrical stimulation intensity to the pads 270. Specifically, the output control unit 304 outputs a pulse voltage at the frequency Fs (in other words, the maximum frequency or a frequency within from 20 Hz to 60 Hz) according to the instruction from the treatment content setting unit 302.

Typically, the output control unit 304 gradually increases the electrical stimulation intensity and outputs the pulse voltage corresponding to the electrical stimulation intensity at the frequency Fs. The initial value of the electrical stimulation intensity is set to the lowest level (for example, level 1) of the predetermined number of levels (for example, 10 levels). The output control unit 304 raises the level one by one when every predetermined period of time has elapsed and gradually increases the electrical stimulation intensity. Note that the treatment content setting unit 302 may receive an instruction input for electrical stimulation intensity from the user through the input interface 230. In this case, the output control unit 304 outputs the pulse voltage corresponding to the electrical stimulation intensity according to the instruction input at the frequency Fs.

Next, when the pulse voltage is output at the frequency Fs by the output control unit 304, the treatment content setting unit 302 receives input for the electrical stimulation intensity desired by the user. For example, when the treatment content setting unit 302 receives an input of level "6" as the desired electrical stimulation intensity, the level for electrical stimulation intensity in the treatment mode using a sweep waveform is set to "6".

The treatment execution unit 306 applies the treatment pulse voltage to the pads 270. Specifically, the treatment execution unit 306 executes treatment of the treatment site by varying the pulse voltage corresponding to the electrical stimulation intensity desired by the user (for example, level "6") within the frequency range K. Typically, the treatment execution unit 306 varies the frequency of the pulse voltage by sweeping the frequency in an increasing direction from the minimum frequency (for example, 1 Hz) to the maximum frequency (for example, 250 Hz), then in a decreasing direction from the maximum frequency to the minimum frequency in the frequency range K.

Note that the treatment execution unit 306 may arbitrarily vary the frequency depending on the treatment mode within the frequency range K.

Processing Procedure

Figure 6:
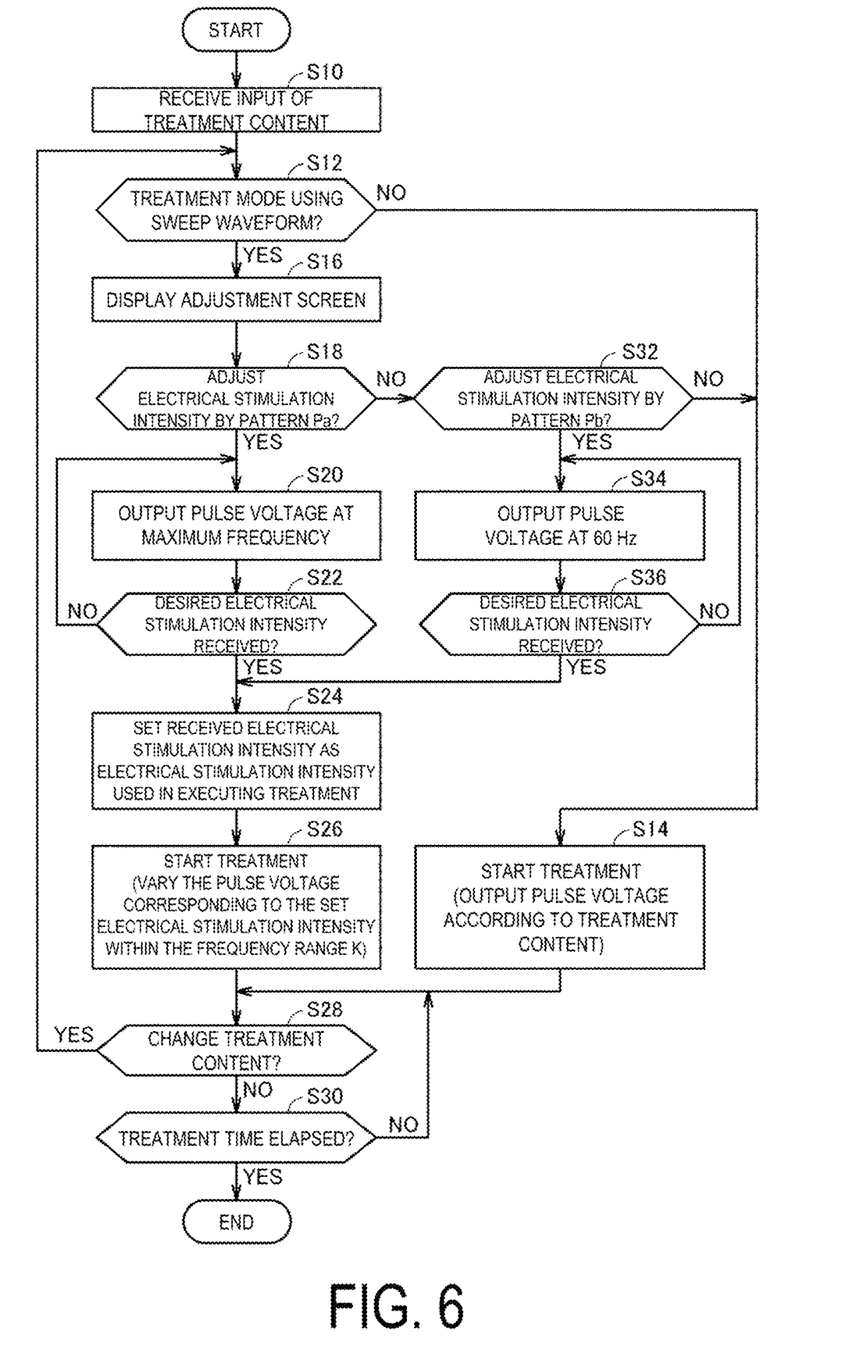
FIG. 6 is a flowchart illustrating an example of a processing procedure of the electrical treatment device according to the first embodiment.

FIG. 6 is a flowchart illustrating an example of a processing procedure of the electrical treatment device 200 according to the first embodiment. Each step in FIG. 6 is mainly performed by the processor 210 of the electrical treatment device 200.

Referring to FIG. 6, the electrical treatment device 200 receives a setting input of the treatment content through the input interface 230 (step S10). Specifically, the electrical treatment device 200 receives a setting input for the treatment mode and the electrical stimulation intensity.

The electrical treatment device 200 determines whether the received treatment mode is a treatment mode in which the frequency varies within the frequency range K (i.e., uses a sweep waveform) (step S12). When the received treatment mode is not a treatment mode using the sweep waveform (NO in step S12), the electrical treatment device 200 starts treatment (step S14). Specifically, the electrical treatment device 200 outputs a pulse voltage according to the treatment content received in treatment step S10. Then, the processing of step S28 described below is executed.

When the received treatment mode is a treatment mode using the sweep waveform (YES in step S12), the electrical treatment device 200 displays the adjustment screen for electrical stimulation intensity on the display 260 (step S16). The adjustment screen is a screen for the user to select whether to adjust the electrical stimulation intensity by either the pattern Pa or the pattern Pb described above.

The electrical treatment device 200 determines whether the electrical stimulation intensity is adjusted by the pattern Pa (step S18). Specifically, the electrical treatment device 200, when the adjustment screen is displayed, determines whether selection of the pattern Pa has been received through the input interface 230.

When selection of the pattern Pa has been received (i.e., adjust the electrical stimulation intensity by the pattern Pa) (YES in step S18), the electrical treatment device 200 outputs a pulse voltage at the maximum frequency within the frequency range K (step S20). Typically, the electrical treatment device 200 gradually increases the electrical stimulation intensity (for example, the amplitude of the pulse voltage) while the pulse frequency is kept at the maximum frequency.

The electrical treatment device 200 determines whether an input of the desired electrical stimulation intensity has been received through the input interface 230 (step S22). When the input has not been received (NO in step S22), then the electrical treatment device 200 executes the processing of step S20. When an input has been received (YES in step S26), the electrical treatment device 200 sets the received electrical stimulation intensity as the electrical stimulation intensity used in executing the treatment (step S24).

The electrical treatment device 200 starts treatment of the treatment site of the user (step S26). Specifically, the electrical treatment device 200 executes treatment of the treatment site by varying the pulse voltage corresponding to the set electrical stimulation intensity within the frequency range K. Note that the electrical treatment device 200 may start the treatment in the case of a start treatment instruction being received through the input interface 230.

Then, the electrical treatment device 200 determines whether a change settings input for changing the settings of the treatment content has been received from the user through the input interface 230 (step S28). When the change settings input has been received (YES in step S28), the electrical treatment device 200 returns to step S12. That is, the electrical treatment device 200 determines whether the treatment mode included in the changed treatment content is a treatment mode using a sweep waveform.

When the change settings input has not been received (NO in step S28), the electrical treatment device 200 determines whether the treatment time has elapsed (step S30). When the treatment time has not elapsed (NO in step S30), then the electrical treatment device 200 returns to step S28. That is, the electrical treatment device 200 continues treatment. When the treatment time has elapsed (YES in step S30), then the electrical treatment device 200 ends the process.

Returning to step S18, when selection of the pattern Pa has not been received (i.e., no adjustment of the electrical stimulation intensity by the pattern Pa) (NO in step S18), the electrical treatment device 200 determines whether to adjust the electrical stimulation intensity by the pattern Pb (step S32).

When selection of the pattern Pb has been received (i.e., adjust the electrical stimulation intensity by the pattern Pb) (YES in step S32), the electrical treatment device 200 outputs a pulse voltage at a frequency within the range of from 20 Hz to 60 Hz (in this example, 60 Hz) (step S34). Typically, the electrical treatment device 200 gradually increases the electrical stimulation intensity while the pulse frequency is kept at 60 Hz. Note that the electrical treatment device 200 may gradually increase the electrical stimulation intensity while repeatedly varying the frequency within the range of from 20 Hz to 60 Hz.

Specifically, the electrical treatment device 200 (output control unit 304) outputs a pulse voltage corresponding to an electrical stimulation intensity A1 (for example, level 1)

while repeatedly varying the frequency within the range of from 20 Hz to 60 Hz in a continuous or step-like manner. Next, the electrical treatment device 200 (output control unit 304) outputs a pulse voltage corresponding to the electrical stimulation intensity A1, then, after a predetermined period of time has elapsed, outputs a pulse voltage corresponding to an electrical stimulation intensity A2 (for example, level 2) that is greater than the electrical stimulation intensity A1 while repeatedly varying the frequency within the range of from 20 Hz to 60 Hz in a continuous or step-like manner. In this way, the electrical treatment device 200 (the output control unit 304) increases the electrical stimulation intensity when each predetermined period of time has elapsed while varying the frequency within the range of from 20 Hz to 60 Hz. This allows the user to set a more appropriate electrical stimulation intensity in the frequency range where muscle contraction is likely to occur.

The electrical treatment device 200 receives an input of the desired electrical stimulation intensity through the input interface 230 (step S36). When the input has not been received (NO in step S36), then the electrical treatment device 200 executes the processing of step S34.

Note that, when selection of the pattern Pb has not been received (i.e., no adjustment of the electrical stimulation intensity by the pattern Pb) (NO in step S32), the electrical treatment device 200 executes the processing of step S14. In this case, the electrical treatment device 200 does not adjust the electrical stimulation intensity described above and performs treatment at the electrical stimulation intensity specified by the user in step S10.

Modified Example

The first embodiment described above has a configuration in which the maximum frequency within the frequency range K or a frequency within the range of from 20 Hz to 60 Hz is used and an electrical stimulation intensity used in a treatment mode using a sweep waveform is set. A modified example of the first embodiment having a configuration in which both the maximum frequency and a frequency within the range of from 20 Hz to 60 Hz are used to set the electrical stimulation intensity will be described.

Referring to FIG. 5, when the treatment mode specified by the user is a treatment mode that uses a pulse voltage with a frequency that varies within the frequency range K, the treatment content setting unit 302 instructs the output control unit 304 to output a pulse voltage at maximum frequency.

Next, when the pulse voltage is output at the maximum frequency F1 by the output control unit 304 according to the instruction, the treatment content setting unit 302 receives input for an electrical stimulation intensity ST desired by the user. The treatment content setting unit 302 instructs the output control unit 304 to output a pulse voltage corresponding to the electrical stimulation intensity ST. The output control unit 304 outputs the pulse voltage corresponding to the electrical stimulation intensity ST at a frequency F2 within from 20 Hz to 60 Hz.

When the pulse voltage corresponding to the electrical stimulation intensity ST is output at the frequency F2, the treatment content setting unit 302 instructs the display control unit 308 to display a permission screen that asks for permission to execute treatment using the electrical stimulation intensity ST. The display control unit 308 causes the display 260 to display the permission screen. The permission screen is a screen prompting the user to select whether to allow or not allow execution of treatment using the electrical stimulation intensity ST to be executed.

When the treatment content setting unit 302 receives instruction to allow execution of the treatment from the user, the electrical stimulation intensity ST is set as the electrical stimulation intensity used in treatment. The treatment execution unit 306 executes treatment of the treatment site by varying the pulse voltage corresponding to the set electrical stimulation intensity within the frequency range K.

Figure 7:
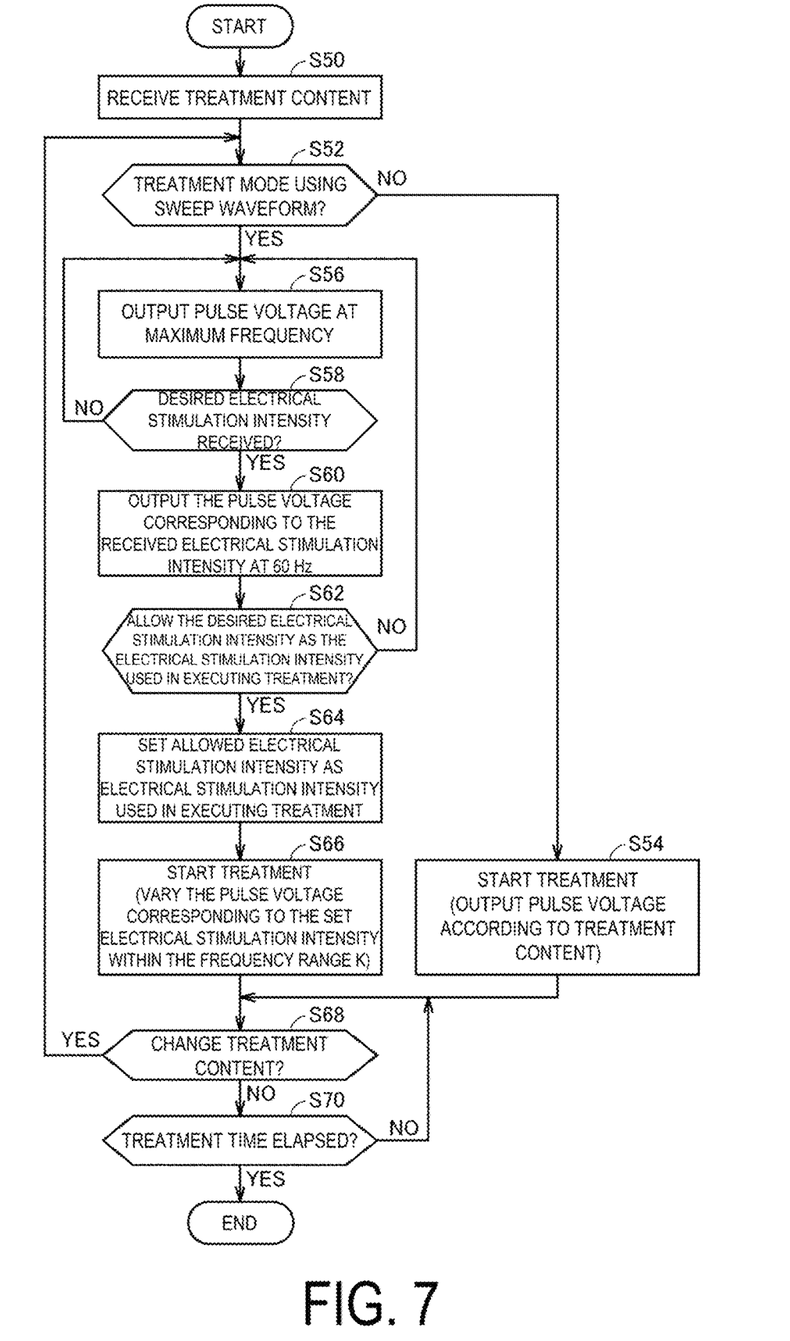
FIG. 7 is a flowchart illustrating an example of a processing procedure of an electrical treatment device according to a modified example of the first embodiment.

FIG. 7 is a flowchart illustrating an example of a processing procedure of the electrical treatment device 200 according to a modified example of the first embodiment. Each step in FIG. 7 is mainly performed by the processor 210 of the electrical treatment device 200.

Referring to FIG. 7, the process at steps S50, S52, and S54 is respectively the same as the process at steps S10, S12, and S14 of FIG. 5, and thus the detailed description thereof is not repeated.

When the received treatment mode is a treatment mode using the sweep waveform (YES in step S52), the electrical treatment device 200 outputs a pulse voltage at the maximum frequency within the frequency range K (step S56). The electrical treatment device 200 determines whether an input of the desired electrical stimulation intensity ST has been received through the input interface 230 (step S58).

When the input has not been received (NO in step S58), then the electrical treatment device 200 executes the processing of step S56. When an input has been received (YES in step S58), the electrical treatment device 200 outputs the pulse voltage corresponding to the electrical stimulation intensity ST at 60 Hz (step S60).

When the electrical treatment device 200 outputs the pulse voltage corresponding to the electrical stimulation intensity ST at 60 Hz, the electrical treatment device 200 determines whether to allow the electrical stimulation intensity ST to be used as the electrical stimulation intensity in executing the treatment (step S62). Typically, the electrical treatment device 200 receives a permission instruction for executing treatment using the electrical stimulation intensity ST through the input interface 230.

When the permission instruction has not been received (i.e., the user does not allow it) (NO in step S62), the electrical treatment device 200 executes the processing of step S56. This allows the user to readjust the electrical stimulation intensity ST. When the permission instruction has been received (YES in step S62), the electrical treatment device 200 sets the allowed electrical stimulation intensity ST as the electrical stimulation intensity used in executing the treatment (step S64).

The electrical treatment device 200 starts treatment of the treatment site of the user (step S66). Specifically, the electrical treatment device 200 executes treatment of the treatment site by varying the pulse voltage corresponding to the set electrical stimulation intensity ST within the frequency range K. The process at steps S68 and S70 is respectively the same as the process at steps S28 and S30 of FIG. 5, and thus the detailed description thereof is not repeated.

Second Embodiment

System Configuration

The first embodiment described above has a configuration in which the user is performed treatment with a single electrical treatment device. A second embodiment having a configuration in which a terminal device and an electrical treatment device are wirelessly connected and the electrical treatment device performs treatment in accordance with an instruction from the terminal device will be described. Note that the terminal device mainly serves as the input interface 230 and the display 260 of the electrical treatment device 200 according to the first embodiment.

Figure 8:
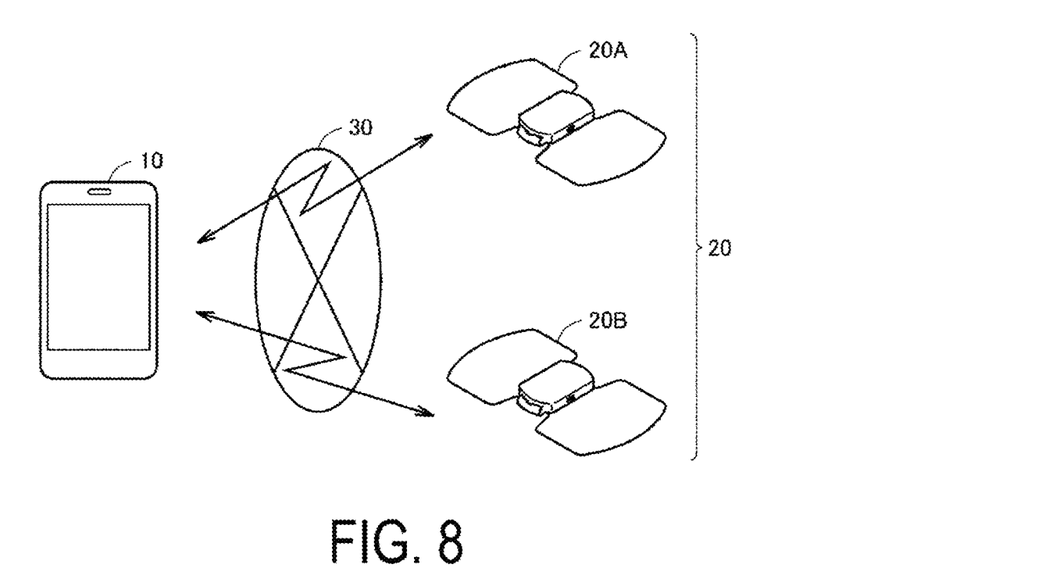
FIG. 8 is a diagram illustrating a schematic configuration of a treatment system according to a second embodiment.

FIG. 8 is a diagram illustrating a schematic configuration of a treatment system 1 according to the second embodiment. Referring to FIG. 8, the treatment system 1 includes a terminal device 10, which is a user terminal, electrical treatment devices 20A, 20B, and a network 30. Hereinafter, when describing configurations and functions shared by the electrical treatment devices 20A, 20B, the electrical treatment devices 20A, 20B are collectively referred to as an "electrical treatment device 20".

The electrical treatment device 20 is a cordless type and includes a pad, a holder, and a main body portion that are united as a single unit when used. These portions are used in combination to perform treatment. The specific configuration of the electrical treatment device 20 will be described later.

The terminal device 10 is, for example, a smart phone including a touch panel. In the description hereinafter, a smartphone will be used as a representative example of the "terminal device". However, the terminal device may be a different terminal device such as a folding type mobile telephone, a tablet terminal device, a personal computer (PC), and a personal data assistance (PDA).

The network 30 for connecting the terminal device 10 and the electrical treatment device 20 employs a short-range wireless communication system, typically Bluetooth (trade name) low energy (BLE). As such, the terminal device 10 and the electrical treatment device 20 are BLE devices having a function of performing wireless communication using BLE. However, the network 30 is not limited thereto, and a different wireless communication system, such as Bluetooth (trade name) or a wireless local area network (LAN), may be employed.

In the treatment system 1 according to the second embodiment, the terminal device 10 gives instructions to the electrical treatment devices 20A and 20B connected in pairing by using an application installed on the terminal device 10. The terminal device 10 displays various kinds of information on a display 158 of the terminal device 10 and notifies the user of necessary information. For example, the terminal device 10 may display information received from the electrical treatment device 20 on the display 158.

Configuration of Electrical Treatment Device 20

Figure 9:
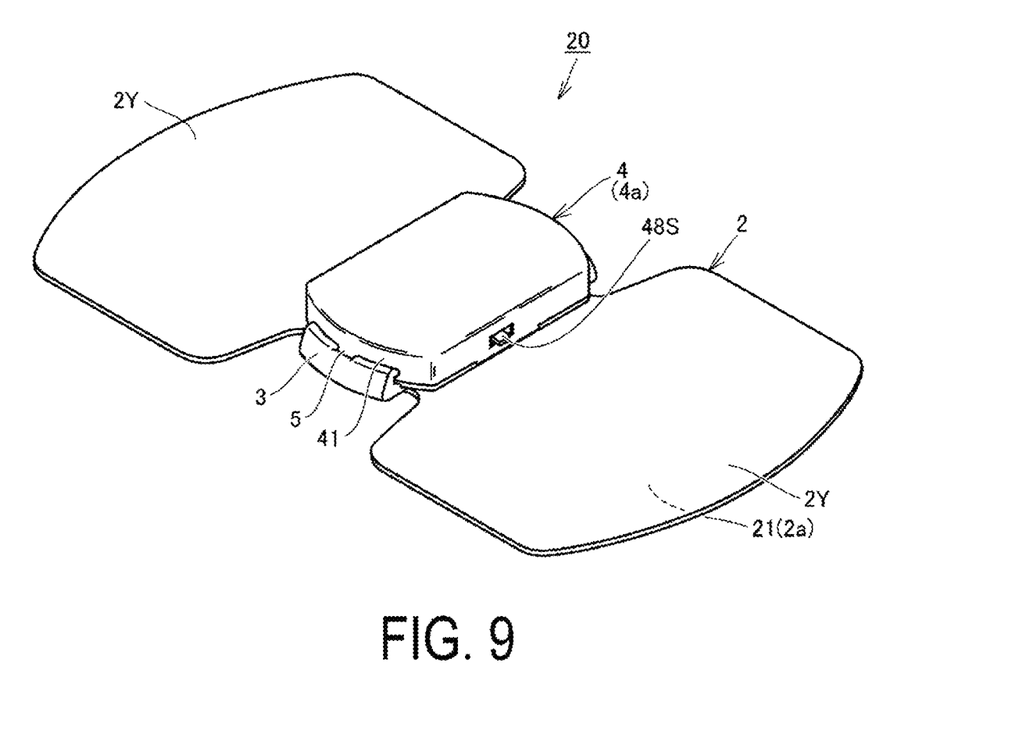
FIG. 9 is a perspective view illustrating an example of the configuration of an electrical treatment device according to the second embodiment.
Figure 10:
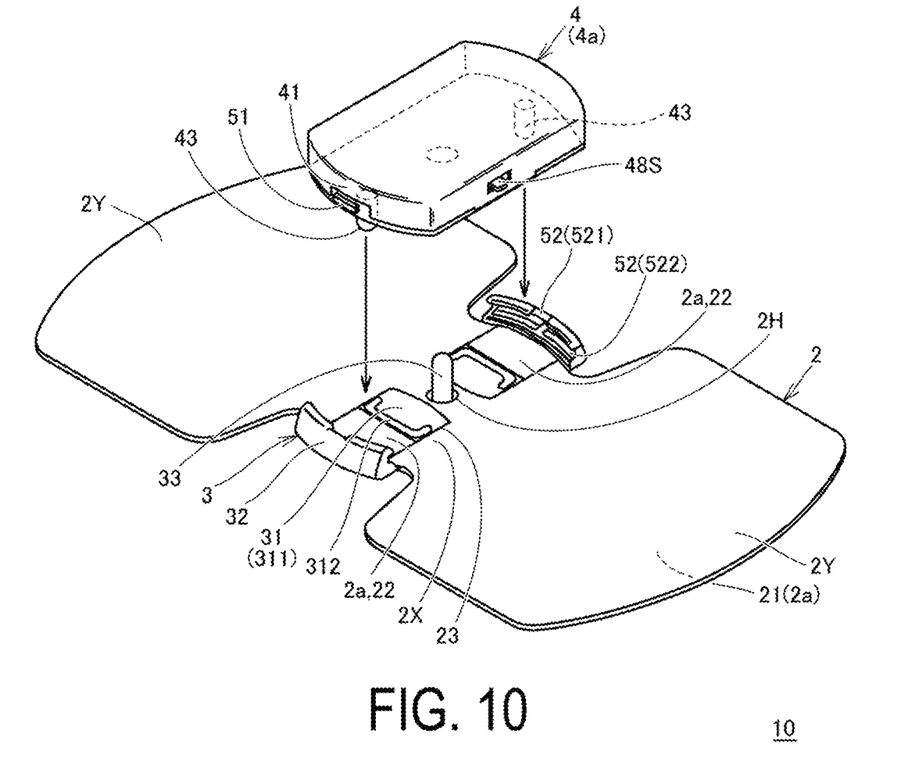
FIG. 10 is a perspective view illustrating a main body portion, a holder, and a pad of the electrical treatment device according to the second embodiment, in a state where the main body portion is separated from the holder and the pad.

FIG. 9 is a perspective view illustrating an example of the configuration of the electrical treatment device 20 according to the second embodiment. FIG. 10 is a perspective view illustrating a main body portion 4, a holder 3, and a pad 2 of the electrical treatment device 20 according to the second embodiment, in a state where the main body portion 4 is separated from the holder 3 and the pad 2.

Referring to FIG. 9 and FIG. 10, the electrical treatment device 20 is a so-called cordless type low-frequency treatment device and includes the pad 2, the holder 3, and the main body portion 4.

The pad 2 has a sheet-like shape and is configured to attach to the user's body. A conductive layer 2a is provided on a body-side portion 21 surface (lower surface), of the outer surfaces of the pad 2, that faces the body. The pad 2 is stuck to the user's skin by using a conductive gel or the like, and a low-frequency pulse is supplied to the user through the conductive layer 2a.

Referring to FIG. 10, the pad 2 includes an attachment portion 2X and a treatment portion 2Y. The attachment portion 2X is held by the holder 3. A window portion 23 and a through hole 2H are provided at the attachment portion 2X. A positioning protrusion 312 of the holder 3 is disposed on the inside of the window portion 23. An interlock pin 33 of the holder 3 is inserted through the through hole 2H. The treatment portion 2Y is provided on both the left and right sides of the attachment portion 2X, and the conductive layer 2a is exposed on the body-side portion 21 of the treatment portion 2Y.

The conductive layer 2a is also exposed on the surface facing the main body portion 4 at the attachment portion 2X, and the exposed portion constitutes a pad side electrode portion 22. The pad side electrode portion 22 is formed to establish an electrical connection with a main body portion side electrode portion 43, and a conductive layer 2a corresponding to one electrode portion (for example, a positive electrode) is exposed at one end of the attachment portion 2X, and a conductive layer 2a corresponding to another electrode portion (for example, a negative electrode) is exposed at the other end of the attachment portion 2X.

Referring to FIG. 10, the holder 3 includes a pad holding portion 31 with a plate-like shape and a pair of wall portions 32 erected from both ends of the pad holding portion 31. An attachment portion 2X of the pad 2 is disposed on an upper surface 311 of the pad holding portion 31. Double-sided adhesive tape, glue, adhesive, or the like is disposed, as necessary, between the upper surface 311 and the attachment portion 2X.

The positioning protrusion 312 is provided on the pad holding portion 31. By fitting the inner peripheral edge of the window portion 23 provided in the pad 2 to the positioning protrusion 312, the pad 2 can be positioned with respect to the holder 3. The interlock pin 33 is centrally disposed on the pad holding portion 31. When attaching the pad 2 to the holder 3, the interlock pin 33 is inserted into the through hole 2H.

The pad 2 is a consumable item, and the pad 2 can be detachably attached to the main body portion 4, thus allowing replacement of the pad 2. In the present embodiment, the holder 3 holds the pad 2 such that the holder 3 and the pad 2 are united, and the main body portion 4 is configured to be detachably attached to the pad 2 and the holder 3. The pad 2 can be replaced together with the holder 3, or it is also possible to reuse the holder 3 as necessary.

Referring to FIG. 9 and FIG. 10, the main body portion 4 includes as an outer cover a case 4a with a substantially rectangular parallelepiped shape. A guiding/engagement portion 5 (FIG. 9) is formed between the case 4a and the holder 3, and the main body portion 4 (case 4a) is detachably attached to the holder 3. The guiding/engagement portion 5 is constituted by a protrusion 51 (FIG. 10) formed on a side surface 41 of the case 4a and a groove portion 52 (FIG. 10) formed in each of the wall portions 32 of the holder 3.

Referring to FIG. 10, the groove portion 52 includes a vertical groove portion 521 and a lateral groove portion 522. The vertical groove portion 521 is formed in the vertical direction and opens upward. The lateral groove portion 522 is formed in the lateral direction and opens at both ends. When the main body portion 4 is attached to the holder 3, both of the protrusion 51 and the groove portion 52 move closer together in a facing direction and engage together. By rotating and moving the main body portion 4 with respect to the holder 3, the engagement between the two is released, and the main body portion 4 can be removed from the holder 3.

With the main body portion 4 attached to the holder 3, the main body portion 4 supplies a low-frequency pulse current to the conductive layer 2a of the pad 2. Specifically, the main body portion 4 includes a pair of the main body portion side electrode portions 43, a substrate (not illustrated), an electric circuit (not illustrated), and an interlock mechanism (not illustrated). The electric circuit includes various control devices and is mounted on the surface of the substrate.

Examples of the control devices include a processor configured to perform various processes, a memory configured to store programs, data, and the like, a communication interface configured to wirelessly communicate various types of data with the terminal device 10, and a waveform generation/output device configured to boost the power source voltage and generating and outputting a low-frequency pulse current (treatment current).

The substrate, the electric circuit, and the interlock mechanism are provided inside the main body portion 4 (case 4a). A power source (not illustrated) such as a battery is also provided inside the main body portion 4 (case 4a). A switch 48S, a display portion (not illustrated) such as a light emitting diode (LED), and a button (not illustrated) are provided on the outside of the case 4a.

In a state in which the main body portion 4 is attached to the holder 3, an end portion of the main body portion side electrode portion 43 abuts the pad side electrode portion 22. Thus, the main body portion side electrode portion 43 and the pad side electrode portion 22 are electrically connected, whereby the electric circuit can supply a low-frequency pulse current to the pad side electrode portion 22.

Configuration of Terminal Device 10

Figure 11:
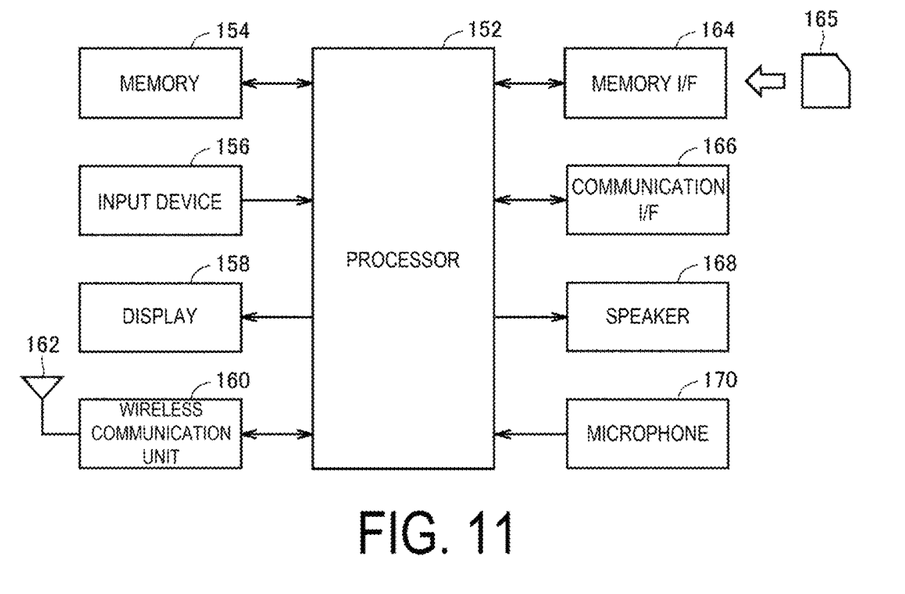
FIG. 11 is a block diagram illustrating an example of a hardware configuration of a terminal device according to the second embodiment.

FIG. 11 is a block diagram illustrating an example of a hardware configuration of the terminal device 10 according to the second embodiment. Referring to FIG. 11, the terminal device 10 includes, as main components, a processor 152, a memory 154, an input device 156, a display 158, a wireless communication unit 160, a memory interface (I/F) 164, a communication interface (I/F) 166, a speaker 168, and a microphone 170.

The processor 152 typically is an arithmetic processing unit such as a central processing unit (CPU) or a multi processing unit (MPU). The memory 154 is realized by random access memory (RAM), read-only memory (ROM), flash memory, and the like.

The input device 156 receives an operation input to the terminal device 10. Typically, the input device 156 is realized by a touch panel. The touch panel is provided on the display 158 that functions as a display portion, and is, for example, an electrostatic capacitive type. The touch panel detects touch operations on the touch panel by an external object at predetermined intervals of time and inputs touch coordinates to the processor 152. However, the input device 156 may include a button or the like.

The wireless communication unit 160 connects to a mobile communication network via a communication antenna 162 and transmits and receives signals for wireless communication. Accordingly, the terminal device 10 can communicate with other communication devices via a mobile communication network such as Long Term Evolution (LTE), for example.

The memory interface 164 reads data from an external storage medium 165. The processor 152 reads the data stored in the storage medium 165 via the memory interface 164 and stores the data in the memory 154. The processor 152 reads the data from the memory 154 and stores the data in the external storage medium 165 via the memory interface 164.

The storage medium 165 may also include media that store programs in a non-volatile manner, such as a compact disc (CD), digital versatile disc (DVD), Blu-ray (trade name) disc (BD), universal serial bus (USB) memory, secure digital (SD) memory card.

The communication interface (I/F) 166 is a communication interface configured to exchange various data between the terminal device 10 and the electrical treatment device 20 and is realized by an adapter, a connector, or the like. As the communication method, for example, a wireless communication method such as Bluetooth low energy (BLE), and wireless LAN may be employed.

The speaker 168 converts an audio signal from the processor 152 to voice and outputs the same to the outside of the terminal device 10. The microphone 170 receives an audio input for the terminal device 10 and provides to the processor 152 an audio signal corresponding to the audio input.

Functional Configuration

The electrical treatment device 20 has the similar configuration with the treatment content setting unit 302, the output control unit 304, and the treatment execution unit 306 in the configuration of the electrical treatment device 200 illustrated in FIG. 5. Each of these units are realized by a control device included in the main body portion 4 of the electrical treatment device 20. The display control unit 308 illustrated in FIG. 5 is realized by the processor 152 of the terminal device 10. In the first embodiment, the user provides various instructions to the electrical treatment device 200 through the input interface 230. In the second embodiment, the user provides various instructions to the terminal device 10 through the input device 156, and the instructions are sent from the terminal device 10 to the electrical treatment device 20. In this way, the various instructions are indirectly provided to the electrical treatment device 20. In other words, the electrical treatment device 20 receives an instruction input from the user through the terminal device 10. More specifically, the electrical treatment device 20 receives an instruction input from a user sent from the terminal device 10 via a communication interface.

Also, the first embodiment has a configuration in which the treatment current flows to the treatment site by a voltage being applied between the electrode of one of the pads 270 with a positive polarity and the electrode of the other pad 270 with a negative polarity. The second embodiment has a configuration in which two electrode portions respectively corresponding to, one having a positive polarity and the other having a negative polarity, are formed on one pad 2, and the treatment current flows to the treatment site by a pulse voltage waveform being applied between the electrodes.

Also, the various information is stored in the memory 220 used by the electrical treatment device 200 for various processes described above in the first embodiment, typically, such information is stored in the memory of the electrical treatment device 20. However, a portion of the information may be stored in the memory 154 of the terminal device 10.

The electrical treatment device 20 has a configuration in which information necessary to notify the user about, information for storing in the terminal device 10, and the like is sent to the terminal device 10. In this way, the terminal device 10 can display on the display 158 a selection screen for the adjustment pattern of the electrical stimulation intensity described above, a permission screen for allowing a treatment using the electrical stimulation intensity ST to be executed, and the like.

Other Embodiments (1) The first embodiment described above has a configuration using the pair of pads 270, but the configuration is not limited thereto. Some embodiments may have a configuration in which an electrode for positive polarity and an electrode for negative polarity are formed on a single pad.

(2) In the embodiments described above, a program may be provided that causes a computer to function and execute controls such as those described in the flowcharts described above. Such a program can also be provided as a program product stored on a non-temporary computer-readable recording medium attached to a computer, such as a flexible disk, a compact disc read only memory (CD), a secondary storage device, a main storage device, and a memory card. Alternatively, a program may be provided, which is stored on a recording medium such as a hard disk built into a computer. The program may also be provided by download via a network.

With the program, required modules from among program modules provided as part of the computer operating system (OS) may be called in a predetermined sequence at a predetermined timing to execute processing. In this case, the modules described above are not included in the program itself, and the process is executed in cooperation with the OS. Programs that do not include such modules may also be included in the program according to the present embodiment.

In addition, the program according to the present embodiment may be provided integrated into a part of a different program. In this case as well, the program according to the present embodiment per se does not include the modules included in the different program described above, and the process is executed in cooperation with the different programs. Such a program integrated in a different program shall also be within the scope of the program according to the present embodiment.

(3) The configuration given as an example of the embodiment described above is an example configuration of the present invention. The configuration can be combined with other known technology, and parts thereof may be omitted or modified within the scope of the present invention. Furthermore, the processes and configurations of other embodiments may be employed as appropriate to the embodiments described above.

Supplement

As described above, the present embodiments include the following disclosure.

Configuration 1

An electrical treatment device (200), includes, a treatment content setting unit (302) configured to set a treatment content specified by a user, a treatment execution unit (306) configured to perform treatment of a site on a body of the user according to the treatment content by controlling a pulse voltage applied to a plurality of electrodes being in contact with the site, and an output control unit (304) configured to output a pulse voltage at a first frequency within a predetermined frequency range before the site being performed the treatment by the treatment execution unit (306), wherein when the pulse voltage at the first frequency is output, the treatment content setting unit (302) receives an input of an electrical stimulation intensity desired by the user, and the treatment execution unit (306) executes the treatment of the site by varying a pulse voltage corresponding to the electrical stimulation intensity desired by the user within the predetermined frequency range.

Configuration 2

The electrical treatment device (200) according to configuration 1, wherein the output control unit (304) gradually increases the electrical stimulation intensity and outputs the pulse voltage corresponding to the electrical stimulation intensity at the first frequency.

Configuration 3

The electrical treatment device (200) according to configuration 1 or 2, wherein the first frequency is a maximum frequency within the predetermined frequency range or a frequency within a range of from 20 Hz to 60 Hz.

Configuration 4

The electrical treatment device (200) according to configuration 1 or 2, wherein when the pulse voltage is output at the first frequency, the treatment content setting unit (302) receives input of a first electrical stimulation intensity desired by the user, and the output control unit (304) outputs a pulse voltage corresponding to the first electrical stimulation intensity at a second frequency within the frequency range, and when a pulse voltage corresponding to the first electrical stimulation intensity is output at the second frequency and execution of treatment of the site using the first electrical stimulation intensity is allowed by the user, the treatment execution unit (306) performs the treatment of the site by varying the pulse voltage corresponding to the first electrical stimulation intensity within the frequency range.

Configuration 5

The electrical treatment device (200) according to configuration 4, wherein the first frequency is a maximum frequency within the predetermined frequency range, and the second frequency is a frequency within a range of from 20 Hz to 60 Hz.

Configuration 6

The electrical treatment device (200) according to any one of configurations 1 to 5, wherein the treatment execution unit (306) varies the frequency of the pulse voltage by sweeping the frequency in an increasing a direction from a minimum frequency to a maximum frequency, then in decreasing direction from the maximum frequency to the minimum frequency in the frequency range.

Configuration 7

The electrical treatment device (200) according to any one of configurations 1 to 6, wherein the electrical treatment device (200) is a low-frequency treatment device.

Configuration 8

A control method for an electrical treatment device (200), including the steps of, setting a treatment content specified by a user, executing treatment of a site on a body of the user according to the treatment content by controlling a pulse voltage applied to a plurality of electrodes being in contact with the site, and outputting a pulse voltage at a first frequency within a predetermined frequency range before the site being performed the treatment in the executing step, wherein when the pulse voltage at the first frequency is output, the setting step includes receiving an input of an electrical stimulation intensity desired by the user, and the executing step includes performing the treatment of the site by varying a pulse voltage corresponding to the electrical stimulation intensity desired by the user within the predetermined frequency range.

Configuration 9

A treatment system (1), including a terminal device (10), and an electrical treatment device (20) configured to be wirelessly communicative with the terminal device, wherein the electrical treatment device (20) includes a treatment content setting unit (302) configured to set a treatment content specified by a user, a treatment execution unit (306) configured to perform treatment of a site on a body of the user according to the treatment content by controlling a pulse voltage applied to a plurality of electrodes being in contact with the site, and an output control unit (304) configured to output a pulse voltage at a first frequency within a predetermined frequency range before the site where the treatment is performed by the treatment execution unit (306), and when the pulse voltage at the first frequency is output, the treatment content setting unit (302) receives an input of an electrical stimulation intensity desired by the user through the terminal device (10), and the treatment execution unit (306) executes the treatment of the site by varying a pulse voltage corresponding to the electrical stimulation intensity desired by the user within the predetermined frequency range.

The embodiments described herein are illustrative in all respects and are not intended as limitations. The scope of the present invention is indicated not by the descriptions above but by the claims and includes all meaning equivalent to the scope and changes within the scope.

REFERENCE SIGNS LIST

1 Treatment system
2, 270 Pad
2H Through hole
2X Attachment portion
2Y Treatment portion
2a Conductive layer
3 Holder
4 Body portion
4a Case
5 Guiding/engagement portion
10 Terminal device
20A, 20B, 200 Electrical treatment device
21 Body-side portion
22 Pad side electrode portion
23 Window portion
30 Network
31 Pad holding portion
32 Wall portion
33 Interlock pin
40 Supporter
41 Side surface
43 Main body portion side electrode portion
48S Switch
51 Protrusion
52 Groove portion
152, 210 Processor
154, 220 Memory
156 Input device
158, 260 Display
160 Wireless communication unit
162 Communication antenna
164 Memory interface
165 Storage medium
168 Speaker
170 Microphone
205 Control device
230 Input interface
240 Power source unit
250 Waveform generation/output device
280 Cord
282 Plug
302 Treatment content setting unit
304 Output control unit
306 Treatment execution unit
308 Display control unit
311 Upper surface
312 Positioning protrusion
521 Vertical groove portion
522 Lateral groove portion

The invention claimed is:

1. An electrical treatment device, comprising:
   a treatment content setting unit configured to set a treatment content specified by a user;
   a treatment execution unit configured to perform treatment of a site on a body of the user according to the treatment content by controlling a pulse voltage applied to a plurality of electrodes being in contact with the site; and
   an output control unit configured to output a pulse voltage at a first frequency within a predetermined frequency range before the treatment at the site is performed by the treatment execution unit, wherein
   when the pulse voltage at the first frequency is output, the treatment content setting unit receives an input of a desired electrical stimulation intensity desired by the user,
   the treatment execution unit executes the treatment of the site by varying a pulse voltage corresponding to the desired electrical stimulation intensity within the predetermined frequency range, and
   the first frequency is a maximum frequency within the predetermined frequency range.

2. The electrical treatment device according to claim 1, wherein
   the output control unit gradually increases an electrical stimulation intensity and outputs the pulse voltage corresponding to the electrical stimulation intensity at the first frequency.

3. The electrical treatment device according to claim 2, wherein
   the output control unit outputs a pulse voltage corresponding to the desired electrical stimulation intensity at a second frequency within the predetermined frequency range, and
   when a pulse voltage corresponding to the desired electrical stimulation intensity is output at the second frequency and execution of treatment of the site using the desired electrical stimulation intensity is allowed by the user, the treatment execution unit performs the treatment of the site by varying the pulse voltage corresponding to the desired electrical stimulation intensity within the frequency range.

4. The electrical treatment device according to claim 2, wherein
   the treatment execution unit varies the frequency of the pulse voltage by sweeping the frequency in an increasing direction from a minimum frequency to a maximum frequency, then in a decreasing direction from the maximum frequency to the minimum frequency in the predetermined frequency range.

5. The electrical treatment device according to claim 2, wherein the electrical treatment device is a low-frequency treatment device.

6. The electrical treatment device according to claim 1, wherein
   the output control unit outputs a pulse voltage corresponding to the desired electrical stimulation intensity at a second frequency within the predetermined frequency range, and
   when a pulse voltage corresponding to the desired electrical stimulation intensity is output at the second frequency and execution of treatment of the site using the desired electrical stimulation intensity is allowed by the user, the treatment execution unit performs the treatment of the site by varying the pulse voltage corresponding to the desired electrical stimulation intensity within the frequency range.

7. The electrical treatment device according to claim 6, wherein
the second frequency is a frequency within a range of from 20 Hz to 60 Hz.

8. The electrical treatment device according to claim 7, wherein
the treatment execution unit varies the frequency of the pulse voltage by sweeping the frequency in an increasing direction from a minimum frequency to a maximum frequency, then in a decreasing direction from the maximum frequency to the minimum frequency in the predetermined frequency range.

9. The electrical treatment device according to claim 7, wherein the electrical treatment device is a low-frequency treatment device.

10. The electrical treatment device according to claim 6, wherein
the treatment execution unit varies the frequency of the pulse voltage by sweeping the frequency in an increasing direction from a minimum frequency to a maximum frequency, then in a decreasing direction from the maximum frequency to the minimum frequency in the predetermined frequency range.

11. The electrical treatment device according to claim 6, wherein the electrical treatment device is a low-frequency treatment device.

12. The electrical treatment device according to claim 1, wherein
the treatment execution unit varies the frequency of the pulse voltage by sweeping the frequency in an increasing direction from a minimum frequency to a maximum frequency within the predetermined frequency range, and in a decreasing direction from the maximum frequency to the minimum frequency within the predetermined frequency range.

13. The electrical treatment device according to claim 12, wherein the electrical treatment device is a low-frequency treatment device.

14. The electrical treatment device according to claim 1, wherein the electrical treatment device is a low-frequency treatment device.

15. A control method for an electrical treatment device comprising the steps of:
setting a treatment content specified by a user;
executing treatment of a site on a body of the user according to the treatment content by controlling a pulse voltage applied to a plurality of electrodes being in contact with the site; and
outputting a pulse voltage at a first frequency within a predetermined frequency range before the treatment at the site is performed in the executing step, wherein
when the pulse voltage at the first frequency is output, the setting step includes receiving an input of a desired electrical stimulation intensity desired by the user,
the executing step includes performing the treatment of the site by varying a pulse voltage corresponding to the desired electrical stimulation intensity within the predetermined frequency range, and
the first frequency is a maximum frequency within the predetermined frequency range.

16. A treatment system, comprising:
a terminal device; and
an electrical treatment device configured to be wirelessly communicative with the terminal device, wherein
the electrical treatment device includes
a treatment content setting unit configured to set a treatment content specified by a user,
a treatment execution unit configured to perform treatment of a site on a body of the user according to the treatment content by controlling a pulse voltage applied to a plurality of electrodes being in contact with the site, and
an output control unit configured to output a pulse voltage at a first frequency within a predetermined frequency range before the treatment at the site is performed by the treatment execution unit,
when the pulse voltage at the first frequency is output, the treatment content setting unit receives an input of a desired electrical stimulation intensity desired by the user through the terminal device,
the treatment execution unit executes the treatment of the site by varying a pulse voltage corresponding to the desired electrical stimulation intensity within the predetermined frequency range, and
the first frequency is a maximum frequency within the predetermined frequency range.

* * * * *